United States Patent
Khairkhahan et al.

(10) Patent No.: US 6,179,809 B1
(45) Date of Patent: Jan. 30, 2001

(54) DRUG DELIVERY CATHETER WITH TIP ALIGNMENT

(75) Inventors: Alexander Khairkhahan, Palo Alto; Michael J. Horzewski; Stuart D. Harman, both of San Jose; Richard L. Mueller, Byron; Douglas R. Murphy-Chutorian, Palo Alto, all of CA (US)

(73) Assignee: Eclipse Surgical Technologies, Inc., Sunnyvale, CA (US)

( * ) Notice: Under 35 U.S.C. 154(b), the term of this patent shall be extended for 0 days.

(21) Appl. No.: 09/156,964

(22) Filed: Sep. 18, 1998

Related U.S. Application Data

(60) Provisional application No. 60/059,892, filed on Sep. 24, 1997.

(51) Int. Cl.$^7$ ............................................... A61M 37/00
(52) U.S. Cl. ............................... 604/95.04; 604/528
(58) Field of Search ........................ 604/95, 523, 525, 604/528, 530, 264, 95.01, 95.04; 600/139, 136, 146, 149, 150, 143

(56) References Cited

U.S. PATENT DOCUMENTS

| | | |
|---|---|---|
| 4,350,148 | 9/1982 | Sivak, Jr. et al. . |
| 4,475,905 | 10/1984 | Himmelstrup . |
| 4,702,260 | 10/1987 | Wang . |
| 4,766,906 | 8/1988 | Wang . |
| 4,784,133 | 11/1988 | Mackin . |
| 4,976,710 | 12/1990 | Mackin . |
| 5,190,050 | 3/1993 | Nitzsche . |
| 5,358,479 | 10/1994 | Wilson . |
| 5,364,352 | * 11/1994 | Cimino et al. ........................ 604/95 |
| 5,378,234 | * 1/1995 | Hammerslag et al. ................ 604/95 |
| 5,464,394 | 11/1995 | Miller et al. . |
| 5,468,233 | 11/1995 | Schraga . |
| 5,489,270 | * 2/1996 | Van Erp ................................ 604/95 |
| 5,498,238 | 3/1996 | Shapland et al. . |
| 5,531,685 | * 7/1996 | Hemmer et al. ...................... 604/95 |
| 5,533,967 | * 7/1996 | Imran ................................... 604/95 |
| 5,554,114 | 9/1996 | Wallace et al. . |
| 5,607,421 | 3/1997 | Jeevanandam et al. . |
| 5,656,029 | * 8/1997 | Imran et al. ..................... 604/528 X |
| 5,656,030 | * 8/1997 | Hunjan et al. ....................... 604/95 |
| 5,697,916 | 12/1997 | Schraga . |
| 5,741,320 | * 4/1998 | Thornton et al. ................ 604/95 X |
| 5,876,373 | * 3/1999 | Giba et al. ........................... 604/95 |
| 5,944,690 | * 8/1999 | Falwell et al. ....................... 604/95 |
| 5,964,757 | 10/1999 | Ponzi ................................... 606/45 |

FOREIGN PATENT DOCUMENTS

WO 99/22655    5/1999    (WO) .

OTHER PUBLICATIONS

Duerig, T.W. and A.R. Pelton, "Structure and Properties of Ti–Ni Alloys," In Press, Titanium Handbook, ASM, 1994.

* cited by examiner

*Primary Examiner*—A. T. Nguyen
(74) *Attorney, Agent, or Firm*—Ilene Lapidus Janofsky; Ross M. Carothers

(57) ABSTRACT

A steerable drug delivery catheter and method of use, particularly adapted for percutaneous use. The distal end of the drug delivery catheter is deflectable. The catheter has a relative movement compensation mechanism for maintaining positioning between the distal end of the drug delivery catheter and the distal end of the drug delivery device therein.

25 Claims, 12 Drawing Sheets

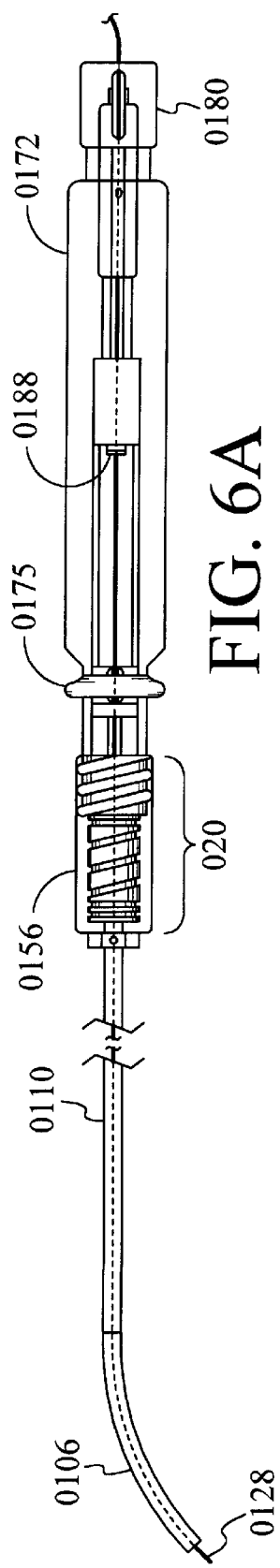
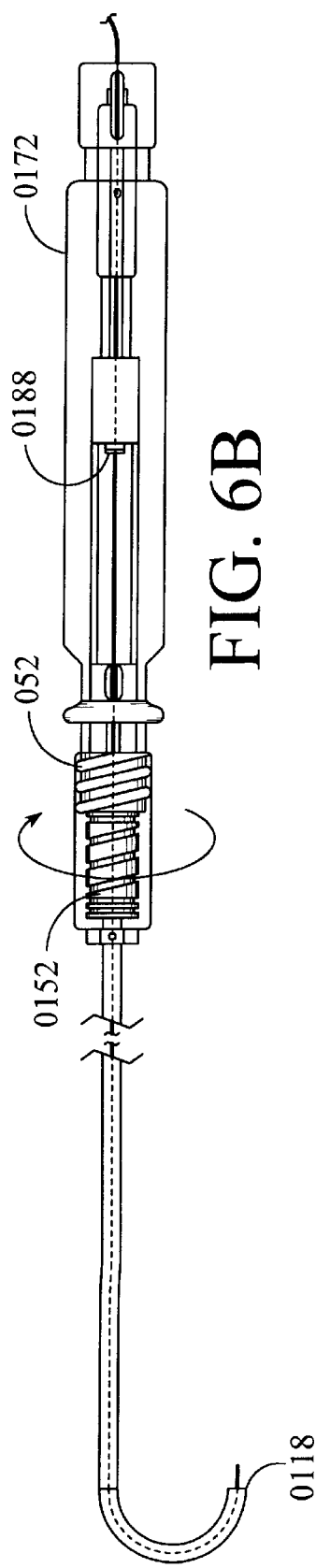
FIG. 6A
FIG. 6B

DRUG DELIVERY CATHETER WITH TIP ALIGNMENT

PRIORITY CLAIM

This Application claims the benefit of domestic priority under 35 U.S.C. section 119(e) from U.S. Provisional Application Serial No. 60/059,892 filed Sep. 24, 1997 entitled FIBER/CATHETER TIP ALIGNMENT, which is herein incorporated by reference in its entirety.

CROSS-REFERENCE TO RELATED APPLICATIONS

This application is related to application Ser. No. 09/156,963, entitled "STEERABLE CATHETER WITH TIP ALIGNMENT AND SURFACE CONTACT DETECTOR", filed simultaneously with the present invention.

FIELD OF INVENTION

The present invention relates generally to drug delivery catheters and catheter procedures involving functional devices. More particularly, the invention relates to a steerable drug delivery catheter and method of use, particularly adapted for percutaneous use. The distal tip of the catheter for guiding a drug delivery device or other functional device extendable there through, is deflectable in at least one given plane. The invention includes an automatic catheter tip alignment system for maintaining constant relative positioning between the distal tip of the functional device and the distal tip of the steerable drug delivery catheter.

BACKGROUND OF INVENTION

The human heart is a muscular dual pump that beats continuously throughout life sending blood to the lungs and the rest of the body. The interior of the heart consists of four distinct chambers. The septum, a thick central muscular wall, divides the cavity into right and left halves. On the right side, the upper half is known as the right atrium. Deoxygenated blood from the rest of the body arrives in the right atrium via the vena cava, the blood is pumped across a one-way valve known as the tricuspid valve into the lower portion known as the right ventricle. From there the blood circulates to the lungs through the pulmonary valve via the pulmonary artery where it is oxygenated by circulation through the alveoli of the lungs (not shown). The blood returns via the pulmonary veins to the left atrium and flows through a second valve, the mitral valve into the left ventricle where it is pumped via the aorta to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

Though the heart supplies blood to all other parts of the body, the heart itself has relatively little communication with the oxygenated blood supply. Thus, the two coronary arteries, the left coronary artery and the right coronary artery, arise from the aorta and encircle the heart muscle on either side "like a crown" to supply the heart itself with blood.

Heart disorders are a common cause of death in developed countries. They also impair the quality of life of millions of people and restrict activity by causing pain, breathlessness, fatigue, fainting spells and anxiety. The major cause of heart disease in developed countries is impaired blood supply. The coronary arteries become narrowed due to atherosclerosis and part of the heart muscle is deprived of oxygen and other nutrients. The resulting ischemia or blockage can lead to angina pectoris, a pain in the chest, arms or jaw due to lack of oxygen to the heart's myocardium, infarction or tissue necrosis in myocardial tissue.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve clots) can be very effective. If drug treatment fails, transluminal angioplasty is often indicated - the narrowed part of the artery, clogged with atherosclerotic plaque or other deposits, can be stretched apart by passing a balloon to the site and gently inflating it a certain degree. In the event drug therapy is ineffective or angioplasty is too risky (introduction of a balloon in an occluded artery can cause portions of the atherosclerotic material to become dislodged which may cause a total blockage at a point downstream of the subject occlusion, thereby requiring emergency procedures), the procedure known as coronary artery bypass grafting (CABG) is the most common and successful major heart operation performed, with over 500,000 procedures done annually in America alone. A length of vein is removed from another part of the body. The section of vein is first sewn to the aorta and then sewn onto a coronary artery at a place such that oxygenated blood can flow directly into the heart. CABG typically is performed in an open chest surgical procedure, although recent advances suggest minimally invasive surgery (MIS) techniques may also be used.

Other less intrusive treatments include angioplasty and the use of stents.

Another method of improving myocardial blood supply is called myocardial revascularization, the creation of channels in the myocardium of the heart (TMR), or creation of channels form the endocardium into myocardium (PTMR).

Percutaneous catheter procedures are typically less traumatic to the patient compared to surgical procedures and offers an alternative solution to persons who are not candidates for surgical procedures. Percutaneous procedures require the ability to steer a catheter apparatus through the vasculature and maneuver the apparatus at the selected site without the undue stress of a lengthy procedure.

U.S. Pat. No. 5,190,050 issued Mar. 2, 1993 to Nitzsche teaches a steerable catheter with a handle and a tube, the distal tip of which may be selectively curved by controllably moving one of three flat, sandwiched shims relative to the others by manipulation of a handle portion.

U.S. Pat. No. 5,358,479 issued Oct. 25, 1994 to Wilson, incorporated herein in its entirety by reference, teaches another steerable catheter with a handle and an inner tube, the apparatus having a single elongated, substantially flat shim spring mounted within the tip of the catheter tube, the shim having at least one transverse or lateral twist which causes the tip of the catheter tube to assume a desired curvature.

Drug therapies with angiogenic growth factors may expedite and/or augment collateral artery development. U.S. Pat. No. 5,498,238 issued Mar. 12, 1996 to Shapland et al., discloses a method of simultaneous angioplasty and drug delivery to localized portions of arteries. The patent teaches the use of an expandable balloon end type catheter which can be filled with a drug-containing fluid and which is allowed to permeate through a semi-permeable membrane of the balloon-tip end and thereby be delivered directly to the surface of arteriosclerotic lesions on stenosed arteries.

A great deal of published scientific information concerning therapeutic agents is currently available on the internet. One company, Annual Reviews is located at http://www.annurev.org. A list of genetically engineered and/or naturally occurring drugs or other agents having pharmacological, therapeutic, diagnostic or other utility is located at http://www.annurev.org/sup/im/im15/im15b.htm. Additional scientific information is available at http://darwin.bio.uci.edu/~cchughes/index.html.

Drug devices also include viewing devices for cardiac interventional procedures. U.S. Pat. No. 4,784,133 issued Nov. 15, 1988 and U.S. Pat. No. 4,976,710 issued Dec. 11, 1990, both to Mackin, both teach of a flexible angioscope/bronchoscope device with an inflatable balloon structure for viewing intravasculature structures. These flexible catheter devices include a ported working channel for introduction of a working device and positioning of the working device at the viewing/treatment distal end.

U.S. Pat. No. 4,350,148 issued Sep. 21, 1982 to Sivak, Jr. et al. also teaches of a drug injector device, in this case for treating esophageal varices. A flexible shafted endoscope has a conduit with distal ended needle is inserted in the endoscope's biopsy channel for effectuating the treatment.

Drug regulating injection mechanisms such as those shown in U.S. Pat. No. 4,475,905 issued Oct. 9, 1984 to Himmelstrup, U.S. Pat. No. 5,468,233 issued Nov. 21, 1995 to Schraga and U.S. Pat. No. 5,697,916 issued Dec. 16, 1997 also to Schraga which teach of devices for regulating drug delivery using a syringe with mechanisms for controlling plunger operation for metered dosages.

U.S. Pat. No. 4,702,260 issued Oct. 27, 1987 and U.S. Pat. No. 4,766,906 issued Aug. 30, 1988, both to Wang, teach bronchoscopic needle assemblies. The needle assemblies are especially adapted for safe and efficacious collection of biopsy samples.

U.S. Pat. No. 5,554,114 issued Sep. 10, 1996 to Wallace et al. teaches an infusion device with preformed shape. An infusion guidewire or catheter is used for introduction of the device through a selected path in a patient's vascular system. An elongated tubular diffusion body lies at the distal end of an elongated tube, the diffusion portion having a plurality of infusion ports through which blood, drug, diagnostic agent or other material can be delivered to the particular site in the vascular system.

U.S. Pat. No. 5,464,394 issued Nov. 7, 1995 to Miller et al. teaches a multilumen percutaneous angioscopy catheter which allows simultaneous irrigation and passage of an angioscope there through.

The use of superelastic and/or shape memory materials is widely known. *Structure and Properties of Ti—NI Alloys: Nitinol Devices & Components*, Duerig et al., In Press, Titanium Handbook, ASM (1994) In general, binary compositions of Nickel (Ni) and Titanium (Ti), yield alloys with shape memory and superelastic properties. These alloys are commonly referred to as Ni—Ti, nitinol, and other industry names. Their precise physical and other properties of interest are extremely sensitive to the precise Ni/Ti ratio used. Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at. % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in pre-stressed materials.

For the purposes of this disclosure, a distinction between superelastic materials and shape memory materials is made. Superelasticity refers to the highly exaggerated elasticity, or springback, observed in many Ni—Ti alloys deformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. With regard to the present invention, it will be understood that the transition temperature of materials must, in general, be somewhat above body temperature.

Thus, there is a need to provide a steerable percutaneous drug delivery catheter which provides controlled catheter deflection for needle placement and alignment of the drug delivery and catheter tips.

ADVANTAGES AND SUMMARY OF INVENTION

Thus, it is an advantage of the present invention to provide a steerable drug delivery catheter and method of use for percutaneous and other intra-vascular procedures.

The present invention teaches a percutaneous drug delivery catheter comprising a catheter jacket having proximal and distal ends, and at least a first lumen, at least a first drug delivery device within the first lumen of the catheter jacket, the drug delivery device having proximal and distal ends, a deflection mechanism at the proximal end of the catheter jacket, the deflection mechanism operatively attached to a deflector device at the distal end of the catheter jacket, activation of the deflector device by movement of the deflection mechanism deflects the distal end of the catheter jacket and the drug delivery device therein, and a relative movement compensation mechanism for maintaining alignment between the catheter jacket and the drug delivery device whereby movement of the deflecting mechanism causes simultaneous compensating movement of the relative movement compensation mechanism.

It is a further advantage of the present invention to provide a catheter capable of being steered and deflected that can maintain tip alignment during deflection of the distal section of the catheter.

It is yet a further advantage of the present invention to provide a percutaneous steerable catheter which can be positioned securely into a selected position in the body.

BRIEF DESCRIPTION OF THE DRAWINGS

FIG. 5AA is an enlarged view of detail 5A.

FIG. 5BB is an enlarged view of detail 5B.

FIGS. 6A and 6B are representative isometric cutaway views of the steerable drug delivery catheter of the present invention illustrating a preferred embodiment of the method of the present invention.

DETAILED DESCRIPTION

Figure 1:
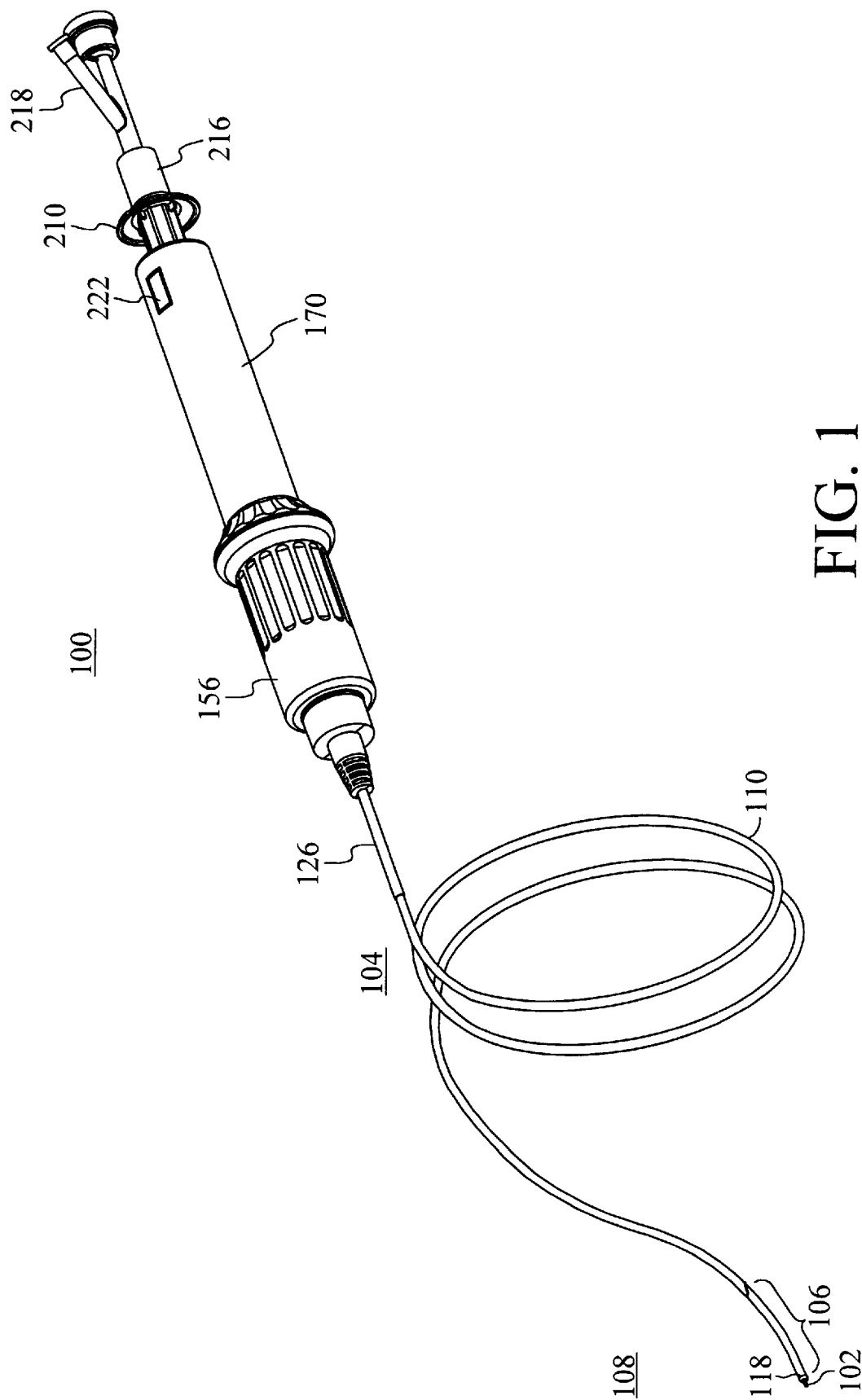
FIG. 1 is a representative isometric view of a preferred embodiment of the steerable drug delivery catheter of the present invention showing a handle having an actuator and deflective end portion.

FIG. 1 is a representative isometric view of a preferred embodiment of the steerable drug delivery catheter 100 of the present invention showing a handle having an actuator 156 and deflective end portion 106 with the distal tip of a functional device 102. A preferred embodiment of the catheter 100 has a handle 170 at its proximal end 104 and a controllably deflectable end portion 106 at its distal end 108. The deflectable end portion 106 is more flexible than the elongated catheter jacket 110, allowing the deflectable end portion 106 to develop a controlled bend with a small radius of curvature.

Components for effectuating multiple degrees of freedom of the distal tip of the catheter as well as other features for steerable catheter systems are disclosed in U.S. patent application Ser. No. 08/833,352 entitled STEERABLE CATHETER by Giba et al. filed Apr. 4, 1997, now U.S. Pat. No. 5,876,373, which is hereby incorporated by reference in its entirety.

Figure 2:
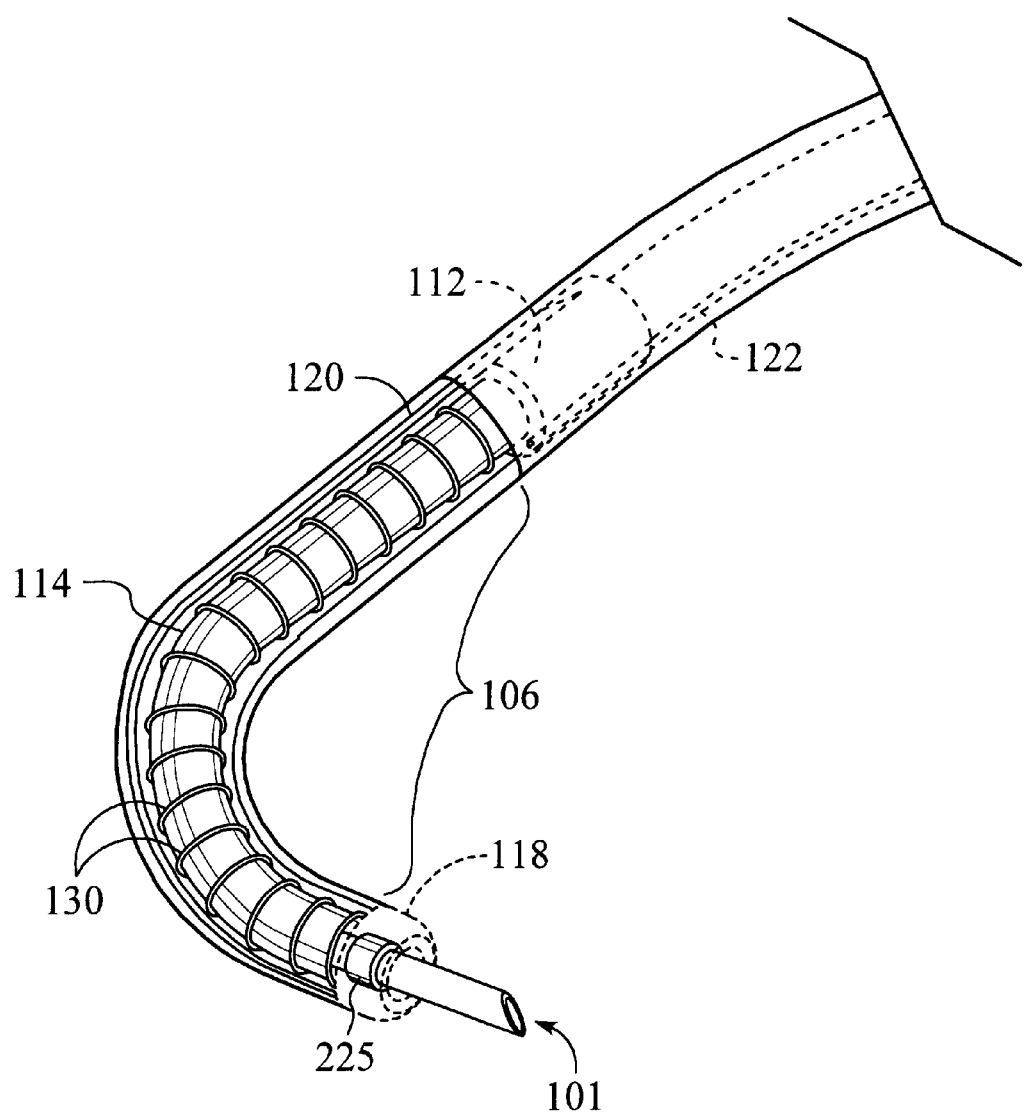
FIG. 2 is a representative partial cutaway view of the deflectable end portion and anchor sleeve of a preferred embodiment of the steerable drug delivery catheter system of the present invention.

FIG. 2 is a representative partial cutaway view of the deflectable end portion 106 and anchor sleeve 112 of a preferred embodiment of the steerable drug delivery catheter 100 of the present invention. As will be understood by the drawings and description herein, the curvature in the deflectable end portion 106 of the inner tube 114 can be deflected as desired. The helical coil spring 130 can be constructed with varying degrees of flexibility, and with any number of coils, such that the curvature can be moved closer to the catheter tip 118 of the inner tube 114 or closer to the anchor sleeve 112. As will be understood, increasing the tension in pull cable 122, attached at a location near the catheter tip 118, by retraction thereof will cause deflection of the catheter tip 118 and the deflectable end portion 106 in a direction essentially out of, and into and toward a position perpendicular to the plane of the shim 120. Continued retraction of the pull cable 122 will cause continued deflection of the catheter tip 118 and deflection of end portion 106 of the steerable drug delivery catheter, with useful ranges of deflection between about 0 and about 180 degrees (U shape) to about 270 degrees (pig-tail shape), or more or less depending upon construction. Drug delivery needle 101 is shown extended from the distal tip of the catheter 118.

As is shown in FIG. 2, an optional ring member 225 may be affixed to drug delivery needle 101 at a predetermined length from the distal end of needle 101. The ring member 225 is constructed with an outer diameter which is greater than the inner diameter of the catheter tip 118 opening. Thus, as the needle 101 is moved out through the catheter tip 118, the ring member 225 engages the catheter tip 118 acting as a mechanical stop and preventing the needle 101 from penetrating matter beyond the predetermined length.

Figure 3:
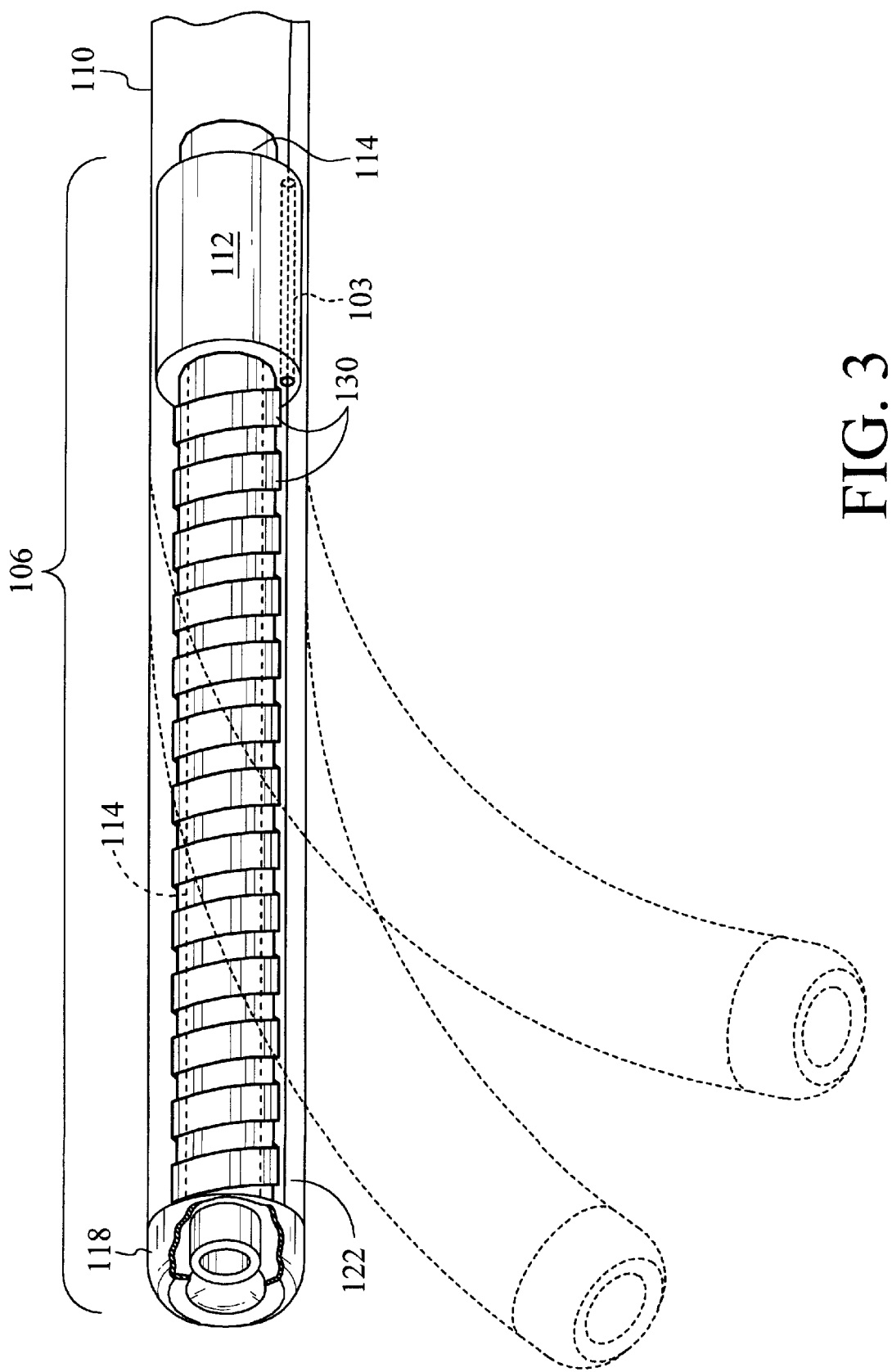
FIG. 3 is a representative partial cutaway view of the deflectable end portion and anchor sleeve of another preferred embodiment of the steerable drug delivery catheter of the present invention.

FIG. 3 is a representative partial cutaway view of the deflectable end portion 106 and anchor sleeve 112 of another preferred embodiment of the steerable drug delivery catheter 100 of the present invention. Pull cable 122 is attached at a location near the tip 118 and extends through pull cable guide 103. The deflectable end portion 106 is made out of a softer material than the proximal shaft catheter jacket 110. As the pull cable 122 is pulled, a force is applied to the catheter tip 118 resulting in tip deflection as shown in the phantom views. This design relies upon the flexibility of the spring 130 to provide the necessary return force instead of a shim as in the design shown in FIG. 2. The spring 130 in any of these figures may be made of various materials known to those of skill in the art including, but not limited to, stainless steel, tungsten, or even partially or completely constructed of one or more superealstic and/or shape memory materials. Cross section of wire of the spring may be for example, oval, round, rectangular or flat ribbon.

Figure 4:
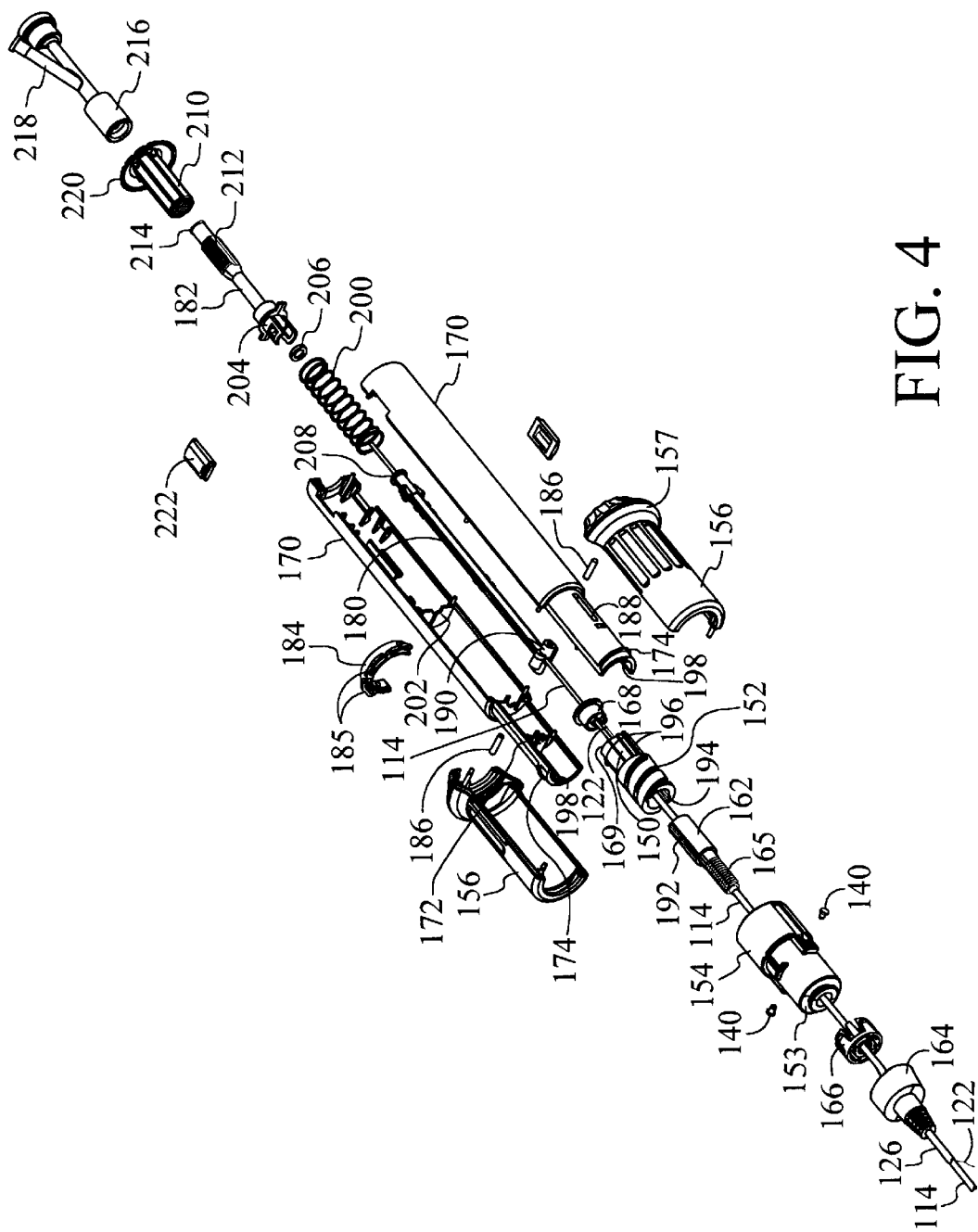
FIG. 4 is a representative exploded view of the internal assembly of a preferred embodiment of the handle of the steerable drug delivery catheter of the present invention using a rotatable relative movement compensation mechanism with an integrated functional device advance mechanism for achieving auto-alignment of the distal tip of the catheter and functional device.

FIG. 4 is a representative exploded view of the internal assembly of a preferred embodiment of the handle of the steerable drug delivery catheter of the present invention using a rotatable relative movement compensation mechanism with an integrated functional device advance mechanism for achieving auto-alignment of the distal tip of the catheter and functional device.

Figure 5A:
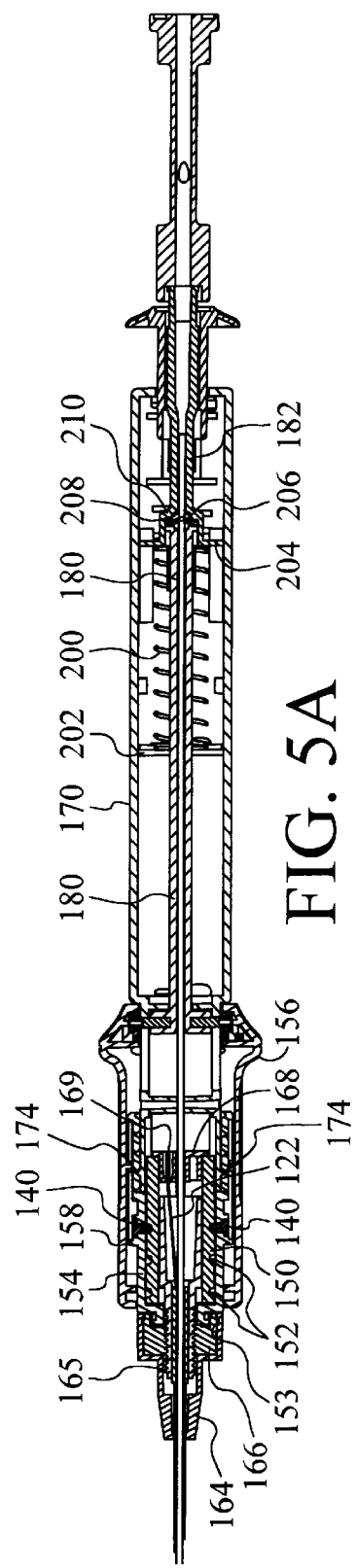
FIG. 5A is a representative sectional view of a preferred embodiment of the handle of the steerable drug delivery catheter of the present invention using a rotatable relative movement compensation mechanism with an integrated functional device advance mechanism for achieving auto-alignment of the distal tip of the catheter and functional device in an un-deflected position.
Figure 5A:
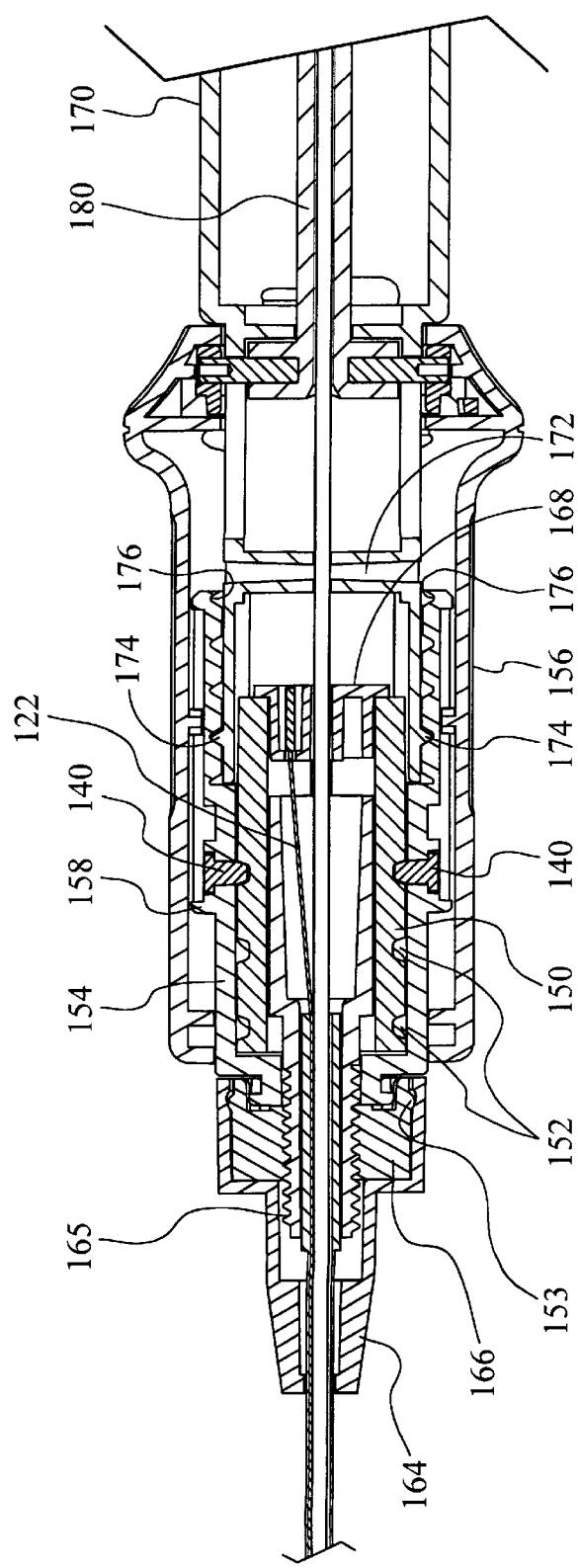

FIG. 5A is a representative sectional view of a preferred embodiment of the handle of the steerable drug delivery catheter of the present invention using a rotatable relative movement compensation mechanism with an integrated functional device advance mechanism for achieving auto-alignment of the distal end of the catheter and functional device. FIG. 5AA is an enlarged view of detail 5A.

Figure 5B:
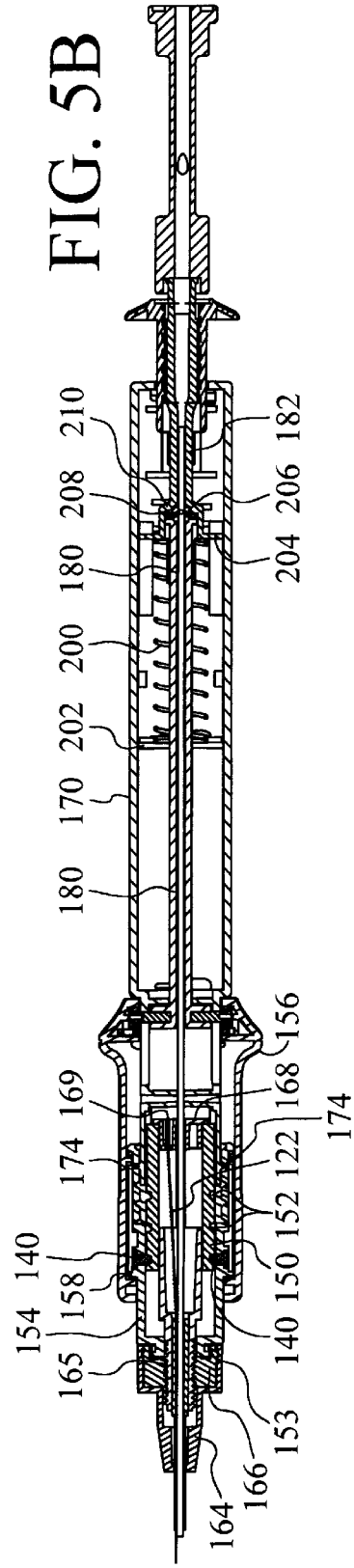
FIG. 5B is a representative section view of a preferred embodiment of the handle of the teerable drug delivery catheter of the present invention using a rotatable relative movement ompensation mechanism with an integrated functional device advance mechanism for achieving auto-alignment of the distal tip of the catheter and functional device in a deflected position.
Figure 5B:
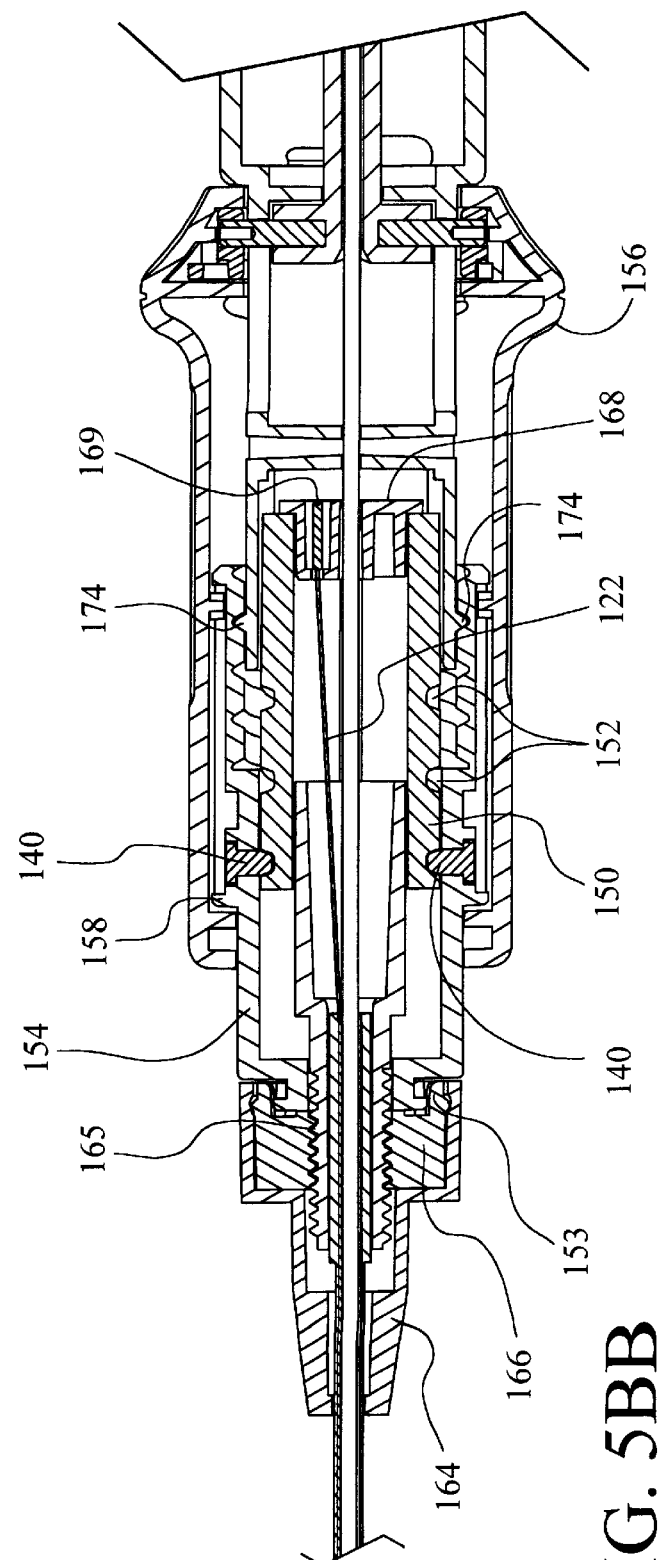

FIG. 5B is a representative section view of a preferred embodiment of the handle of the steerable drug delivery catheter of the present invention using a rotatable relative movement compensation mechanism with an integrated functional device advance mechanism for achieving auto-alignment of the distal end of the catheter and functional device in a deflected position. FIG. 5BB is an enlarged view of detail 5B.

As seen in FIGS. 4 and 5 outer catheter jacket 110 terminates at its proximal end 126 and is coupled to catheter base 162. Proximal hub 166 is contained within the catheter boot 164 and threads over inside stepped and threaded portion 165 of catheter base 162. The proximal hub 166 is coupled to a distal flange portion 153 of inner deflection knob 154. Deflection actuator 150 slides over catheter base 162 and has an external helical grooved portion 152 located distally on the deflection actuator 150. Two pins 140 attached to inner deflection knob 154 engage helical groove 152, thus rotation of inner deflection knob 154 about deflection actuator 150 translates into linear motion between inner deflection knob 154 and deflection actuator 150. An actuator 156 (shown in two sections in FIG. 5) couples radially around the inner deflection knob 154 and translates linearly with respect to inner deflection knob 154. The actuator 156 engages inner deflection knob 154 at flange 158.

The inner tube 114 is attached to handle 170 at coupling point 172. A distal external, helical rib or thread 174 on the handle 170 fits into and acts in cooperation with an operatively pitched and contoured internal helical slot or groove 176 located proximally on the inner deflection knob 154. The inner tube 114 continues proximally, sliding through a front tube 180 and terminates within a back tube 182. A bushing 184 is mounted on bushing pins 186 which extend through longitudinal slots 188 located distally within handle 170 and extend into pin seats 190 located distally on front tube 180. Thus, as the front tube 180 is moved linearly with respect to the handle 170, the bushing pins 186 move linearly within slots 188.

Relative motion between the front tube 180 and the handle 170 is limited to linear motion; there is no rotational motion between the front tube 180 and the handle 170 as such is prevented by the bushing pins 186 which only slide linearly in slots 188. Similarly, axially and longitudinally extending ribs or keys 192 located proximally and externally on catheter base 162 slide linearly within correspondingly shaped linear grooves 194 located internally and distally on deflection actuator 150 opposite the external helical groove 152, thus preventing rotational motion as between the catheter base 162 and the deflection actuator 150. Finally, axially and longitudinally extending ribs or keys 196 located proximally and externally on deflection actuator 150 slide linearly within correspondingly shaped linear grooves 198 located internally and distally on handle 170 at a point distal to slots 188, thus preventing rotational motion as between the deflection actuator 150 and the handle 170.

Pull cable 122, such as shown in FIGS. 2 and 3, extends proximally from the catheter tip 118 through the catheter base 162 and through the deflection actuator 150, and terminates at pull cable stop 168. Pull cable 122 biases pull cable stop 168 against the proximal end 169 of deflection actuator 150.

The actuator 156 rotates around the bushing 184 and the entire assembly including the actuator 156, the bushing 184, bushing pins 186 seated in the front tube 180 along with the front tube 180, back tube 182 and proximal assembly all translate linearly. Additionally, as the actuator 156 is rotated about a central axis, the inner deflection knob 154 is co-operatively and simultaneously similarly rotated thus effectuating linear translation of deflection actuator 150 and thereby increasing tension in pull cable 122. To prevent the contractive forces on the pull cable 122 which deflect the catheter 100 and translate into counter-rotational forces on the actuator 156 from actually causing the assembly to essentially "unwind", therefore, bushing 184 is constructed with several detents 185 which compress between actuator 156 and handle 170 distally. In a preferred embodiment of the bushing 184, therefore, the resilient detents 185 are distributed around the bushing 184 so as to engage one or more correspondingly shaped grooves, indentations within the proximal flange 157 on actuator 156.

Therefore, as the actuator 156 is rotated in a first direction so as to cause deflection of the deflectable portion 106 of the catheter 100, engagement of the detents 185 of the bushing 184 within the proximal flange 157 of the actuator 156 provides an indexed mechanism, which allows a tactile response by the physician so as to control or at least be aware of the degree of deflection caused by said rotation of the actuator 156. Furthermore, engagement of the detents 185 of the bushing 184 within the proximal flange 157 of the actuator 156 prevents uncontrolled counter-rotation caused by the above described contractive forces developed in the pull cable 122 of the deflected catheter 100. Upon intentional counter-rotation by the physician, resilient detents 185 deform and allow rotation of the actuator 156 as desired. Thus, bushing 184 is designed with resilient detents 185 which provide directionality, i.e., they provide a certain degree of resistant to rotational forces on the actuator 156 intended to deflect the catheter 100 but provide an increased resistance to counter-rotational forces, thereby providing an indexed mechanism with tactile response upon rotation in either direction.

The handle 170 retains a portion of the back tube 182, the back tube 182 slidable through the handle 170 and biased proximally by spring member 200; the spring member 200 is retained between standing rib member 202 extending internally from handle 170 and distal flange 204 on back tube 182. A sealing member 206 is placed between a proximal flange 208 on the front tube 180 and the distal flange 204 on the back tube 182. A depth stop 210 is threaded onto external helical threads 212 of back tube 182 extending proximally from handle 170. A Luer fitting 214 or other suitable coupling and sealing device is useful for coupling a Touhy-Borst type fitting 216 to the back tube 182. A drug delivery device may be coupled securely to the Touhy-Borst type fitting 216 and be advanced through the back tube 182 and into the inner tube 114. A saline flush, drug solution, visualization or other therapeutic agent containing fluid can be provided to the steerable drug delivery catheter via one branched arm 218 of fitting 216. In a preferred embodiment, it will be understood that any backflow preventer, check valve, blood seal, etc. with the necessary operative function and suitability can be employed elsewhere on the steerable drug delivery catheter 100 and will be included within the scope of the present invention.

During a percutaneous procedure using a steerable drug delivery catheter as shown in FIG. 1, maintaining alignment between the tip of the drug delivery device 101 and catheter tip 118 is preferred for controlling advance of the drug delivery device.

FIGS. 6A and 6B show an automatic tip alignment mechanism for a steerable drug delivery catheter system using a differential screw mechanism or relative movement compensation mechanism 020 within deflection knob 0156. The differential screw member within the knob 0156 has two differing thread pitches where threads 0152 effectuate tip deflection and threads 052 effectuate tip alignment compensation. When the deflection knob 0156 is turned, a corresponding advancement or retraction of the catheter's outer jacket occurs causing handle section 0172 to move in relation to the proximal region of center or inner tube 0114 and the drug delivery device thereby maintaining drug delivery device alignment. FIGS. 6A and 6B show the sequential deflection of the distal tip section as the deflection knob 0156 is turned. FIG.6A shows the catheter distal section 0106 out advance, FIG. 6B shows the distal section 0106 deflected 101. The diaphragm valve 0188 acts as a seal component to prevent saline solution, if used, from being emitted from the handle while still allowing translation of the drug delivery device. A drug delivery is inserted into the inner tube 0114 and the distal tip 0101 of the drug delivery device and catheter tip 0118 (as shown in FIG.1) are adjusted and aligned manually prior to use. As the deflectable tip section 0106 is deflected as shown in FIG. 6B, the differential screw in deflection knob 0156 causes relative motion of the catheter jacket 0110 and handle 0172 that is attached to the advance mechanism thereby maintaining the alignment between the drug delivery device distal tip 0101 and catheter tip 0118 with the improved auto-alignment knob incorporated in the handle 0172.

Figures 6D, 6E:
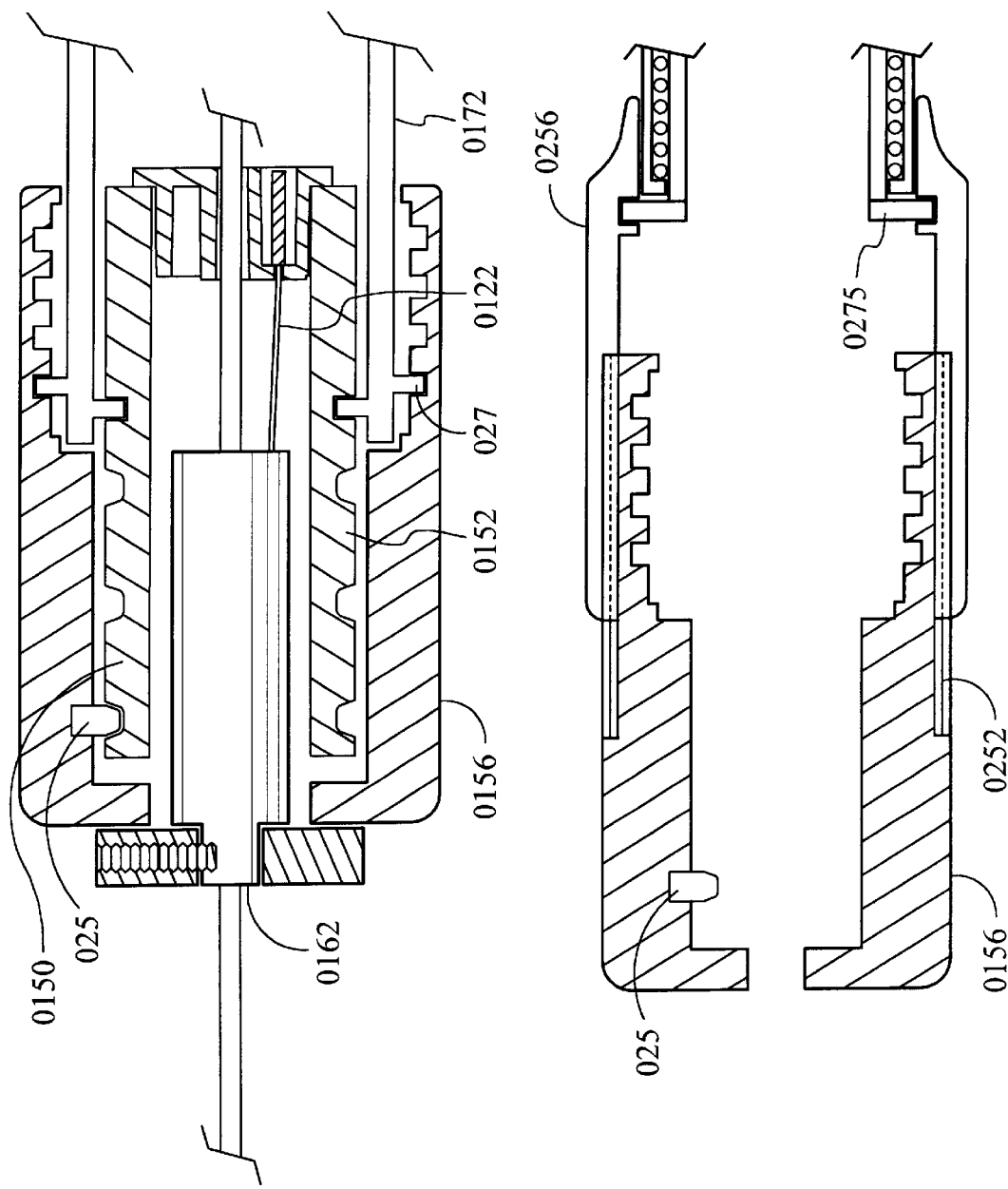
FIG. 6D is a partial cut-away view of a second embodiment of the handle using a rotatable relative movement compensation mechanism showing advance and deflection components for achieving auto-alignment.
FIG. 6E is a cross-sectional view of a variation of the embodiment shown in FIGS. 6D–E and 6A of the handle device using an integrated rotatable differential screw with an integrated advance mechanism for achieving auto-alignment.

FIG. 6D shows a cross-sectional view of the deflection knob 0156 with the catheter base 0162. The threads 0152 for effectuating deflection of the catheter's distal end 0118 are engaged by a pin 025 attached to the deflection knob 0156. The tip alignment compensation threads 052 inside proximal section of the deflection knob 0156 are engaged by another pin 027 attached to the deflection housing tube 0150. The pull wire 0122 is attached at a stop connected to the deflection housing tube 0150. When the deflection knob 0156 is turned, the deflection housing tube 0150 translates over the catheter base 0162. The threads create linear translation compensation of the drug delivery distal tip 0101 as the catheter tip 0118 is deflected.

FIG. 6E is a cross-sectional view of a variation of the embodiment shown in FIGS. 6A, 6B and 6D using an integrated rotatable differential screw mechanism in deflection knob 0156 that further includes an integrated advance component thereby allowing a physician to maintain hand placement while adjusting the amount of deflection by knob 0156 or while advancing. The design shown in FIG.6E in cross-section further includes an advance annular knob 0256 that slides over and rotates with the deflection knob 0156. This sliding aspect is achieved by longitudinal slots 0252 in the outer surface of the deflection knob 0156 and corresponding longitudinal slots in the annular knob 0256. The advance annular knob 0256 replaces the advance knob 0175 shown in FIGS. 6A, B and D above. Rotation of the advance knob 0256 rotates the deflection knob 0156. Linear advancement of the advance knob 0256 alone without rotation of the deflection knob 0156 advances without tip deflection due to the longitudinal slots 0252 in the deflection knob 0156 guiding longitudinal slots in the advance knob 0256. Advancement is achieved through a advance collar 0275 that is attached to the advance slider. The advance knob 0256 has a return spring 0276.

Figure 6F:
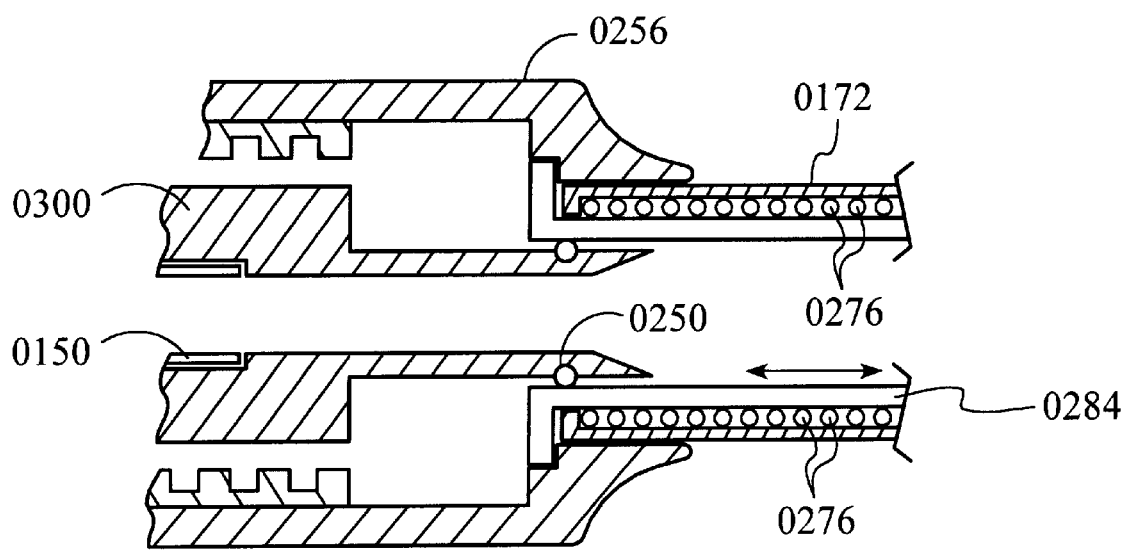
FIG. 6F is a cross-sectional view of a variation of an O-ring sealing member for the drug delivery device for the design shown in FIGS. 6D–E.

FIG. 6F is a cross-sectional view of an alternate design for the functional requirements of the diaphragm valve 0188 sealing device for use with the catheter handle concepts shown in FIGS. 6A, B, D and E. The sealing device is an O-ring 0250 that is disposed about a central member 0300 where the drug delivery device translates within the central member 0300. This central member 0300 is attached to the deflection housing tube 0150. An annular extension member 0284 is attached to the advance slider 0184 shown in FIG. 6B and slides along on the external side of O-ring 0250 to maintain the fluid seal. An equivalent sealing member of O-ring 0250 is a quad seal. The O-ring seal operates comparable to a "syringe" type device.

The following description of the mechanical operation of the steerable drug delivery catheter 100 of the present invention is intended for illustrative purposes only, and is not to be construed in any way as limiting the scope of subject matter claimed herein. Reference is made to all of the figures.

As described above, the steerable drug delivery catheter of the present invention has a tip deflection mechanism as well as a functional device tip alignment mechanism. With regard to FIGS. 4 and 6A–6B, rotation of the actuator 156 in a clockwise direction, i.e., as viewed from a proximal end, will effect corresponding rotation of inner deflection knob 154. Since the actuator 156 and inner deflection knob 154 are rotated relative to the handle 170, and the catheter base 162 is keyed to the deflection actuator 150 by ribs 192 engaging grooves 194 along with the deflection actuator 150 being keyed to the handle 170 by ribs 196 sliding into grooves 198 thereby preventing rotational motion as between the handle 170, the deflection actuator 150 and the catheter base 162, said clockwise rotation will cause proximal translation of deflection actuator 150 by pins 140 riding in helical groove 152, as deflection actuator 150 is moved linearly in a proximal direction, tension in the pull cable 122 acts on the distal tip 118 of the steerable drug delivery catheter 100 and causes deflection thereof.

Operation of the automatic functional device tip alignment mechanism is based on a screw thread pitch differential. Without the tip alignment feature of the present invention as deflection of the deflectable portion 106 of the steerable drug delivery catheter 100 occurs the orientation of the distal tip 118 of the catheter 100 and the distal tip 102 of the functional device would be modified such that any pre-existing alignment would be lost. The cause of this loss of alignment between the distal tip 118 of the catheter 100 and the distal tip 102 of the functional device upon deflection of the deflectable portion 106 is caused by retraction of the pull cable 122, causing an apparent change in the length of the elongated catheter jacket 110 and a displacement of any pre-existing alignment between the distal tip 118 of the catheter 100 and the distal tip 102 of the functional device.

Therefore, to compensate for these alignment disrupting forces, screw threads having a differential in pitch size are used. With reference to the drawings, as mentioned above, deflection of the deflectable portion 106 of the catheter 100 is caused by clockwise rotation of the actuator 156 and inner deflection knob 154. Said clockwise rotational motion of actuator 156 and inner deflection knob 154 causes distal linear translation of inner deflection knob 154, proximal hub 166 and catheter base 164 thereby causing compression of the outer catheter jacket 110 and proximal linear translation of deflection actuator 150 and pull cable stop 168 thereby increasing tension in pull cable 122 and causing deflection of the deflecting portion 106. Simultaneously, as will be apparent by an inspection of the drawings, as inner deflection knob 154 is rotated clockwise by actuator 156, external helical thread 174 on the handle 170 engaged by internal helical groove 176 within inner deflection knob 154 causes simultaneous translation of the handle 170, thus slightly moving the drug delivery device and thereby compensating for the effective change in length of the outer catheter jacket 110 by maintaining alignment between the distal tip 118 of the catheter 100 and the distal end of the drug delivery device.

In the case of a percutaneous procedure, intervention occurs when a functional device is advanced through the inner tube 114 of the steerable drug delivery catheter and into the patient. Advance is effected in one of two ways—by manually urging in a distal direction either back flange 220 of depth stop 210 or actuator 156. In either case, the functional device being held firmly in place at the proximal end by Touhy-Borst type fitting 216 advances distally along with the back tube 182 and the front tube 180, both sliding over the inner tube 114, the bushing pins 186 extending from the pin seats 190 in the front tube 180 contained by and riding within the slots 188 located distally on the handle 170, thus placing the spring 200 into increased compression. Retraction of the drug delivery device decreases the compressive forces on the spring 200.

In a preferred embodiment of the steerable drug delivery catheter of the present invention, access port cover plate 222, as shown in FIGS. 1 and 4 can be removed and any operative device, electrical contacts such as thin coaxial or other electrical traces, leads, conductors, etc. can lead through at least the outer catheter sheath and be utilized at any of various positions on the handle 170, elongated portion 110 or distal tip 118 of the steerable drug delivery catheter 100 of the present invention. In particular, the distal tip 118 can be provided with a positioning sensor or visualization device, for providing any of various signals from any of various types of sensor or analyzer equipment, such as the ultrasound ranging methods and devices shown and described in U.S. patent application Ser. No. 08/852,977 filed May. 7, 1997 entitled ULTRASOUND DEVICE FOR AXIAL RANGING which is hereby incorporated herein by reference in its entirety. In a preferred embodiment, an annular ultrasound transducer is positioned distally on the distal tip 118 to transmit ultrasound signals substantially perpendicular to tissue, the transducer further receiving returning signals from the tissue to be treated.

Figure 7:
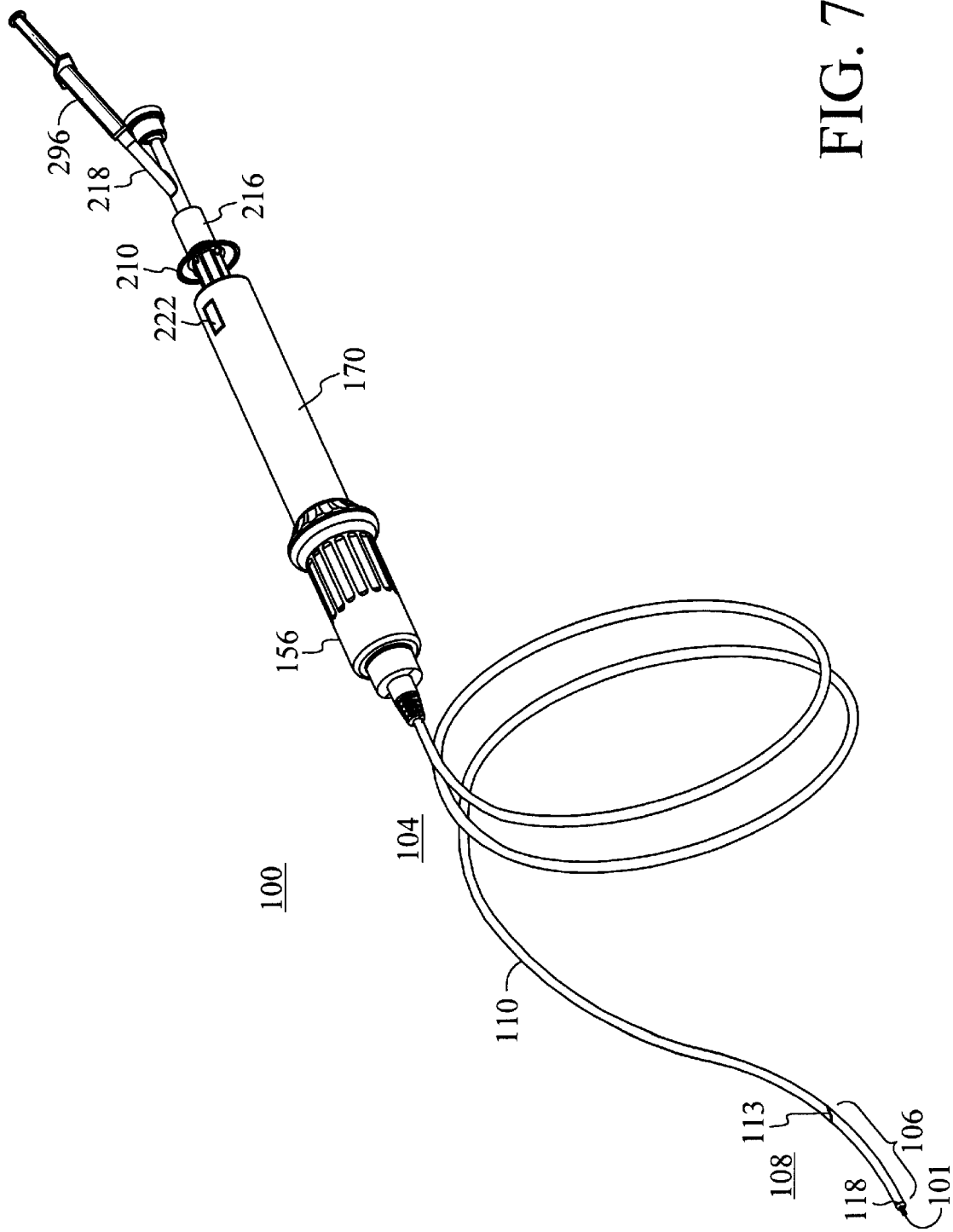
FIG. 7 is a representative isometric view of a drug delivery apparatus coupled to the proximal end of the handle of the steerable drug delivery catheter of the present invention.

FIG. 7 is a representative isometric view of an alternate embodiment of the present invention with a drug delivery apparatus 296 coupled to the proximal end 104 and a drug delivery needle 101 extending beyond the distal end of the steerable drug delivery catheter 100 of the present invention. As shown, other tools or functional devices may be attached to the handle 170 of the steerable drug delivery catheter 100 of the present invention for operation through the inner tube 114 in addition to the drug delivery or dispensing apparatus 296. It will be understood, therefore, that such drug delivery or dispensing apparatus 296 can be manually or automatically activated, can be adjustable or programmable to dispense individual aliquots of a predetermined volume, at a predetermined or specified rate, as desired.

In co-pending application Ser. No. 09/080,175 entitled DRUG DELIVERY MODULE , filed May 16, 1998, and hereby incorporated by reference in its entirety, teaches a drug delivery device with a drug delivery needle for percutaneous catheter based procedures. The elongated portion of the device comprises a single or multi-lumen flexible shaft for containing at least one drug delivery channel in a drug delivery tube. A connector tube extends through a catheter mount and is sealed to a drug conduit. The drug conduit extends through elongated tubular portion of the catheter to the distal tip of the elongated portion where the drug conduit connects to a piercing needle. The piercing needle end portion has a bevel cut end tip or other operable tip for piercing tissue and delivering drug or other compound there through. The drug delivery conduit with piercing needle is inserted through the working channel of the device to treat the desired number of drug delivery tissue sites. The drug flow is communicated from a reservoir through drug conduit and is dispensed through piercing needle subsequent to advance of piercing needle through the distal tip of device. Drugs can be delivered to tissue via advanceable drug conduits with piercing needle tips which pass through a working channel of the instrument.

Figure 8:
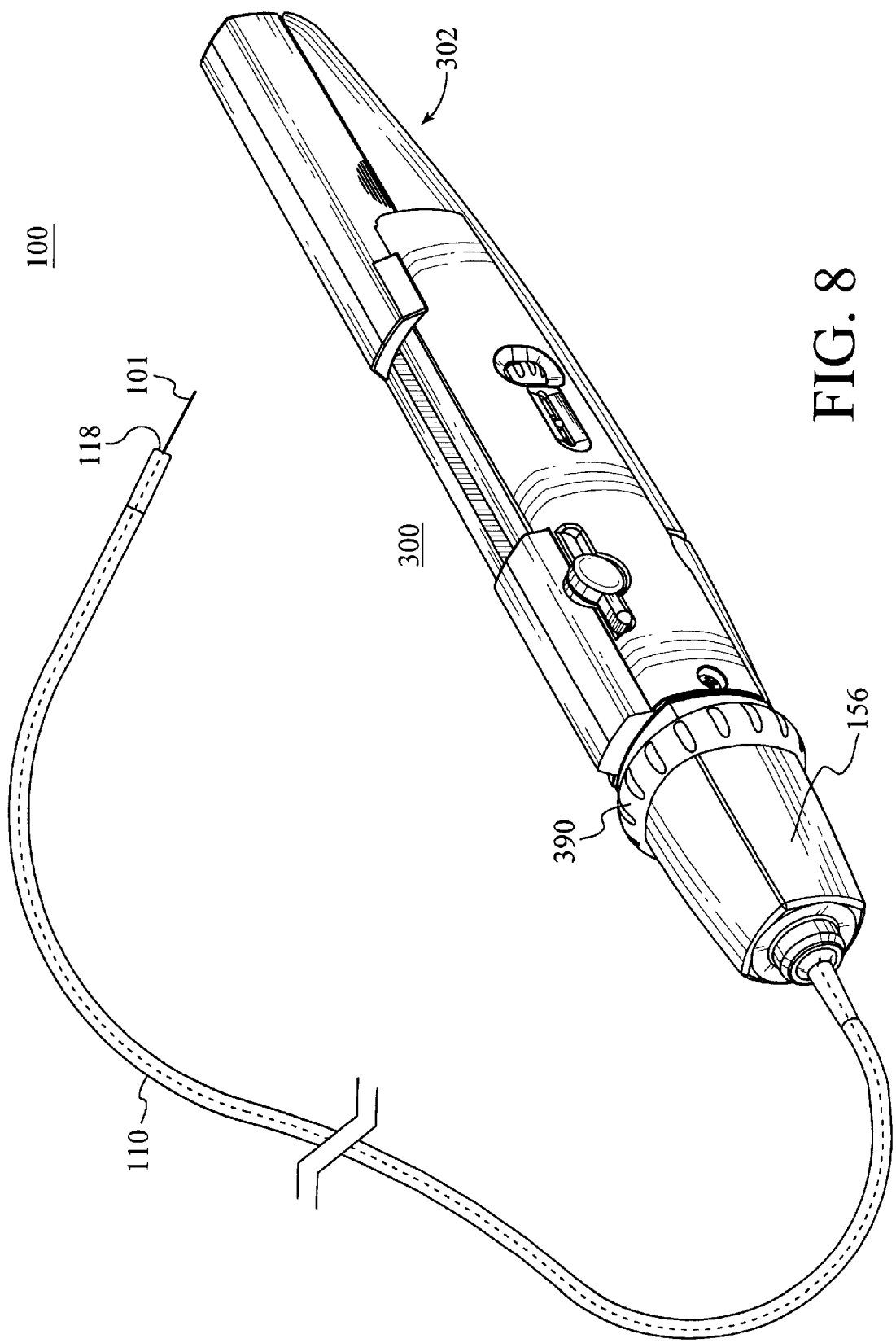
FIG. 8 is a representative isometric view of an alternative embodiment the steerable drug delivery catheter of the present invention with a drug delivery module.

FIG. 8 is a representative view of an alternate embodiment of a steerable drug delivery catheter 100 incorporating an automated drug delivery module 300 of the present invention. The module 300 enables a user to both extend a piercing needle and dispense drug or other agent there through, with a single, manual "draw" or squeeze force applied to a trigger.

The elongated catheter jacket 110 of the drug delivery catheter 100 is a single or multi-lumen containing at least one drug delivery device.

The drug delivery module 300 is attached to the proximal end of the actuator 156. A drug conduit (not shown) extends from module 300 through the elongated catheter jacket 110 to the distal tip of the steerable drug delivery catheter.

It will be understood that elongated catheter jacket 110 may comprise a single lumen or multi-lumen extrusion. In a preferred embodiment, the pull cable 122 (as shown in FIG. 2) is in a separate lumen . Thus, the mechanical steering mechanism is physically separated from the drug conduit thus minimizing the risk of contamination.

Thus, flow of liquid, solid or vapor phase drug, solution or other agent or compound is communicated from the module 300 through the drug conduit and is dispensed through drug delivery needle 101 subsequent to advance of drug delivery needle 101 through the distal tip 118 of device 100. The distal tip 118 of elongated catheter jacket 110 of catheter device 100 can be oriented by actuator 156.

Figure 9:
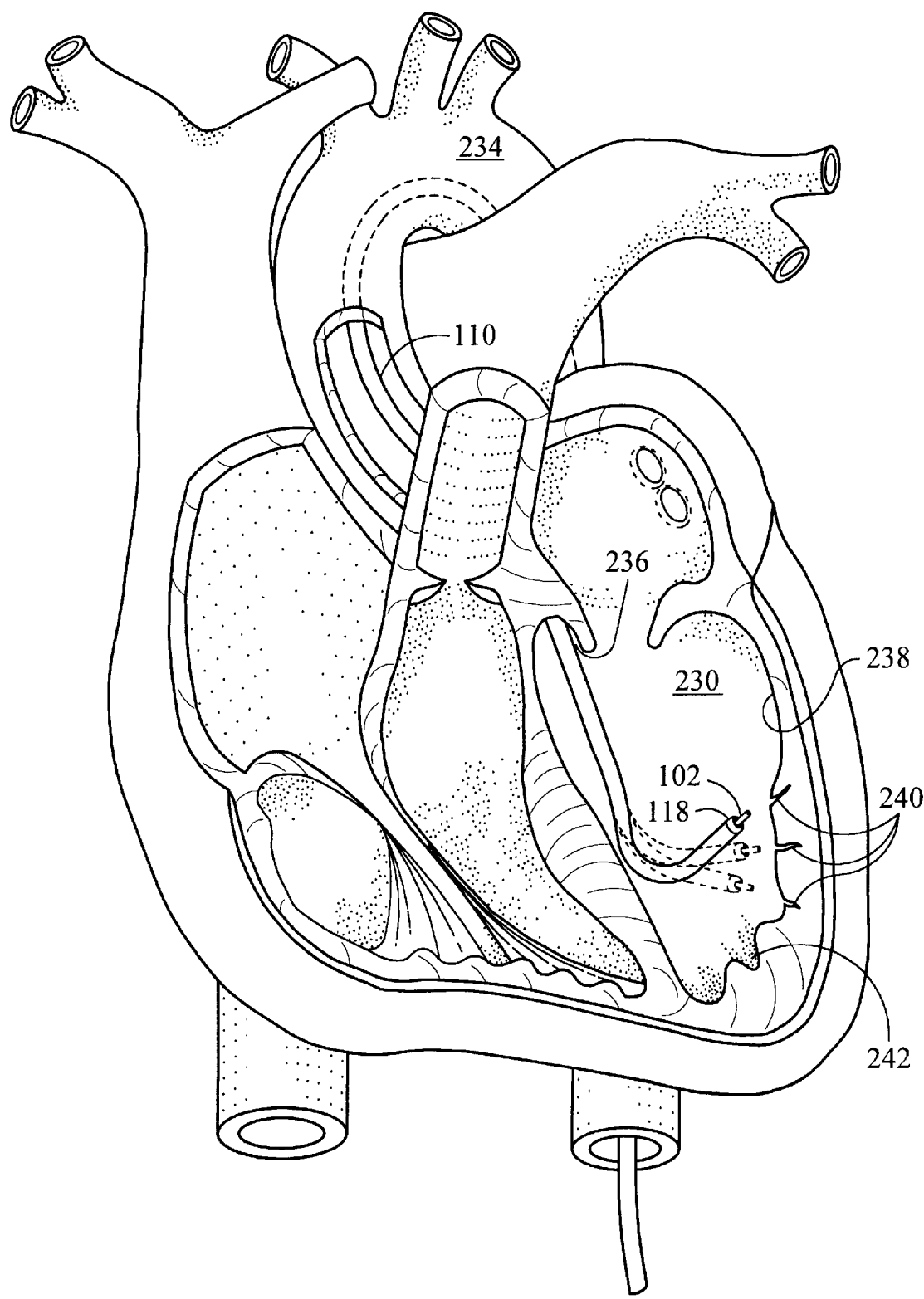
FIG. 9 is a representative perspective view of the steerable drug delivery catheter of the present invention within the left ventricle.

FIG. 9 is a representative perspective view of the steerable drug delivery catheter 100 of the present invention within the left ventricle 230. As indicated above and with regard to the figures, the present invention is directed to catheter systems which are guided into and through parts of the body, such as into the left ventricle, with and without the use of a guide catheter or other guide system. Guide catheter and guidance systems are well known and may be used with the present invention, and therefore are included within the scope of this invention. Typically, entry into the vasculature is made through the femoral artery. A guide wire (not shown) is positioned within the left ventricle 230. The steerable drug delivery catheter 100 is advanced over the guide wire and into the left ventricle 230. The guide wire is retracted out of the steerable drug delivery catheter and the functional device is advanced into position with the steerable drug delivery catheter.

However, a guide wire or guide catheter need not be used. Alternatively, the distal tip 118 and deflectable end portion 106 of the steerable drug delivery catheter 100 is inserted into the patient, extended over the aortic arch 234 and prolapsed through the aortic valve 236 into the left ventricle 230. The steerable drug delivery catheter 100 can be guided into a selected position adjacent a selected surface 238, in this case a portion of endocardium. As the actuator 156 is rotated, deflection of the deflectable portion 106 results in slight modification of the dimension of the elongated catheter jacket 110 of the catheter 100, the modification compensated for by the relative movement compensation mechanism of the present invention. Furthermore, a wall contact detection system provides wall contact and contact pressure information to the physician.

Thus, by sequential deflection the deflectable end portion 106 of the steerable drug delivery catheter 100 and/or by rotation of the steerable drug delivery catheter 100, extending the distal end of a drug delivery device or other functional device there through, delivering drugs or performing other therapy, visualization or diagnostic, and retracting the distal end of the drug delivery device or other functional device back into the deflectable end portion 106, the steerable drug delivery catheter 100 can treat a series of individual, selected treatment points 240 of tissue such as endocardium.

The functional device or devices of the present invention includes those devices for treatment and diagnosis of affected organs, tissues or interiors or interior surfaces of the body, including devices configurable and extendable through one or more lumens within a steerable drug delivery catheter, for example, radio frequency tissue ablation devices, microwave cutters, ultrasound transmitters, mechanical coring devices, fluid jets.

Furthermore, adjunct use of ancillary drug delivery apparatus, blood seal device, depth stop apparatus such as clamps, bushings, etc., visualization device, marker device as well as other hardware and methodology will be considered within the scope of the present invention.

The alignment mechanism or tip alignment mechanism or automatic tip alignment mechanism of the steerable drug delivery catheter can be any relative movement compensation mechanism, including, but not limited to, a screw mechanism, for example, a rotatable differential screw mechanism, gear, camming or threaded mechanism.

For the purposes of the present invention and disclosure herein, the term "drug" or "drugs" includes any and all drugs or therapeutic agents including, but not limited to, antibiotics, vaccines, function regulators, for example, antiarrhythmic drugs, growth factors or other drugs or compounds that can be delivered to the heart, anticoagulant antagonists, Protamine Sulfate, anticoagulants, Heparin, antifibrinolytic, Amicar (aminocaproic acid), platelet inhibitors, ReoPro (abciximab), thrombolytics, Activase (alteplase, TPA), antihistamines, anti-inflammatory agents, Toradol (ketorolac tromethamine), immuno-suppressives, Sandimmune (cyclosporin), receptor antagonists, Tagamet (cimetidine hydrochloride), adrenergic blockers, Minipress (prazosin hydrochloride), adrenergic stimulants, Aldomet (methyldopate HCl), alpha/beta adrenergic blockers, Normodyne (labetalol HCl), angiotensin converting enzyme inhibitors, Capoten (captopril), angiotensin II receptor antagonists, Cozaar (losartan potassium), antiarrhythmics Group I, Norpace (disopyramide phosphate), antiarrhythmics Group II, Brevibloc (esmolol hydrochloride), antiarrhythmics Group III, Cordarone (amiodarone HCl), antiarrhythmics Group IV, Cardizem (diltiazem HCl), beta blockers, Inderal (propranolol HCl), calcium channel blockers, Procardia (nifedipine), diuretics, Bumex (bumetanide), hypertensive emergency agents, Hyperstat (diazoxide), angiogenic agents, FGF-1, FGF-2, EGF, Vascular Endothelial Growth Factor (VEGF) (preclinical), inotropic agents, Lanoxin (digoxin), patent ductus arteriosus therapy, Indocin (indomethacin sodium trihydrate), Rauwolfia derivatives and combinations, Diupres (reserpine-chlorothiazide), vasodilators, Nitrostat (nitroglycerin), vasopressors, Vasoxyl, adjuncts, Kytril (granisetron HCl), androgen inhibitors, Lupron (leuprolide actetate), antibiotic derivatives, Doxorubicin Hydrochloride, antiestrogen, Nolvadex (tamoxifen citrate), antimetabolites, Roferon-A (interferon alfa-2a), cytotoxic agents, Taxol, enzyme inhibitors, Ras farnesyl-transferase inhibitor (preclinical), hormones, Depo-Provera (medroxy-progesterone acetate), immuno-modulators, Proleukin (aldesleukin), nitrogen mustard derivatives, Alkeran (melphalan HCl), agents used in photodynamic therapy, such as photo-active or photo-labile compounds, and/or other materials for performing functions including flushing and cooling, stimulating other responses, detection, analysis, monitoring, visualization or control, etc., said solutions comprising waters, saline and the like, solid and semi-solid materials, and in any forms including capsules and granules, implants, etc. The present invention includes the delivery of liquid, solid or semi-solid, time release formulations, etc. It will be understood that there are additional drugs or therapeutic agents which may become useful, such as agents directed at bone or implanted in semi-permeable sacs, radioisotopes, and future gene therapies.

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action. Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A percutaneous drug delivery catheter comprising:

a catheter jacket, having proximal and distal ends, and at least a first lumen;

at least a first drug delivery device within the first lumen of the catheter jacket, the first drug delivery device having proximal and distal ends;

a deflection mechanism at the proximal end of the catheter, the deflection mechanism operatively attached to a deflector device at the distal end of the catheter jacket, the deflection mechanism comprising a groove portion on a deflection actuator which cooperates with a set of thread pins attached to a rotatable inner deflection knob coupled to the catheter jacket, activation of the deflector device by movement of the deflection mechanism deflects the distal end of the catheter jacket and the drug delivery device therein; and a relative movement compensation mechanism operatively attached to the deflection mechanism and the proximal end of the first drug delivery device, the relative movement compensation mechanism comprising a thread portion on a handle which cooperates with a groove portion on the inner deflection knob, wherein, during movement of the deflection mechanism, simultaneous movement of the relative movement compensation mechanism occurs whereby the alignment between the distal end of the catheter jacket and the distal end of the first drug delivery device is maintained during the deflection.

2. The catheter of claim 1 further comprising an operative device.

3. The catheter of claim 2 wherein the operative device is an ultrasound ranging device.

4. The catheter of claim 1 further comprising an indexing means for limiting the movement of the deflection mechanism with respect to the relative movement compensation mechanism.

5. The catheter of claim 4 further comprising an actuator radially aligned with the deflection knob, wherein the rotation of the actuator results in corresponding rotation of the inner deflection knob and relative linear movement of the deflection actuator and the handle.

6. The catheter of claim 5 wherein the at least first drug delivery device is attached to a coupling device and translates within an inner tube, said inner tube attached to the handle.

7. The catheter of claim 6 wherein the first drug delivery device is advanceable within the inner tube.

8. The catheter of claim 6 wherein the coupling device is branched with at least a first and second arm, the first drug delivery device is coupled through the first arm and a second drug delivery device is coupled through the second arm of the coupling device.

9. The catheter of claim 6 wherein the distal end of the drug delivery device comprises a drug delivery needle.

10. The catheter of claim 9 further comprising an automated drug delivery module, attached to the actuator, enabling extension of the piercing needle and dispensing of at least one therapeutic agent there through.

11. The catheter of claim 10 wherein the drug delivery device is attached to a fluid reservoir.

12. The catheter of claim 11 wherein the fluid reservoir contains at least one therapeutic agent.

13. The catheter of claim 12 wherein the therapeutic agent is an angiogenesis agent.

14. The catheter of claim 12 wherein the fluid reservoir contains saline.

15. The catheter of claim 4 wherein the deflection mechanism further comprises a pull cable, having proximal and distal ends, the distal end of the pull cable attached to the distal end of the catheter jacket and extended through a pull cable guide within an anchor sleeve, the anchor sleeve coupled to the distal end of the inner tube and attached to the catheter jacket, the pull cable further extended through the catheter base and the deflection actuator and attached proximally to a pull cable stop, at the proximal end of the deflection actuator.

16. The catheter of claim 15 wherein the deflection mechanism further comprises a shim, having proximal and distal ends, the proximal end attached to the anchor sleeve and a spring and the distal end of the shim attached to the distal end of the catheter jacket.

17. The catheter of claim 4 further comprising a depth stop threaded to external helical threads of a back tube, the back tube slidably disposed in the handle.

18. The catheter of claim 4 further comprises a sealing member between the back tube and a front tube.

19. A method of treatment within a body using a percutaneous drug delivery catheter, the steps of the method comprising:

a) providing a percutaneous drug delivery catheter that includes, a catheter jacket having proximal and distal ends, at least a first drug delivery device disposed within the catheter jacket, the drug delivery device having proximal and distal ends, a deflection mechanism at the proximal end of the catheter jacket causing deflection of the distal end of the catheter jacket, the deflection mechanism comprising a groove portion on a deflection actuator which cooperates with a set of thread pins attached to a rotatable inner deflection knob coupled to the catheter jacket, and a relative movement compensation mechanism operatively attached to the deflection mechanism and the proximal end of the first drug-delivery device, the relative movement compensation mechanism comprising a thread portion on a handle which cooperates with a groove portion on the inner deflection knob, whereby alignment between the distal end of the catheter jacket and the distal end of the drug delivery device attached to the relative compensation mechanism is maintained during deflection;

b) positioning the catheter for performance of a drug delivery procedure in the body;

c) deflecting the distal end of the catheter jacket with movement of the deflection mechanism causing simultaneous compensating movement of the relative movement compensation mechanism; and d) effectuating delivery of at least one therapeutic agent.

20. The method of claim 19 wherein in step b) the catheter is positioned within a body cavity.

21. The method of claim 19 wherein in step b) the catheter is positioned within the left ventricle.

22. The method of claim 19 step b) further including a guide wire for advancing the device through the vasculature and into position within the body.

23. A steerable percutaneous drug delivery catheter for treating internal body surfaces the apparatus comprising:

a catheter jacket having proximal and distal ends, and at least a first lumen;

at least a first drug delivery device within the first lumen of the catheter jacket, the drug delivery device having proximal and distal ends;

a deflection mechanism, comprising a groove portion on a deflection actuator which cooperates with a set of thread pins attached to a rotatable inner deflection knob, said inner deflection knob operatively coupled to the catheter jacket; and a relative movement compensation mechanism operatively attached to the drug delivery device, the compensation mechanism comprising a thread portion on a handle which cooperates with a groove portion on the inner deflection knob;

whereby movement of the deflection mechanism causes simultaneous compensating movement of the relative movement compensation mechanism.

24. A percutaneous drug delivery catheter comprising:

a catheter jacket, having proximal and distal ends, and at least a first lumen;

at least a first drug delivery device within the first lumen of the catheter jacket, the first drug delivery device having proximal and distal ends;

a deflection mechanism at the proximal end of the catheter, the deflection mechanism operatively attached to a deflector device at the distal end of the catheter jacket, the deflection mechanism comprising a groove portion on a deflection actuator which cooperates with a set of thread pins attached to a rotatable inner deflection knob coupled to the catheter jacket, activation of the deflector device by movement of the deflection mechanism deflects the distal end of the catheter jacket and the drug delivery device therein; and a relative movement compensation means operatively connected to the deflection mechanism and the proximal end of the first drug delivery device for maintaining alignment between the catheter jacket and the drug delivery device, the relative movement compensation means comprising a thread portion on a handle which cooperates with a groove portion on the inner deflection knob, whereby movement of the deflection mechanism causes simultaneous movement of the relative movement compensation means.

25. A catheter with tip alignment comprising:

a catheter jacket having proximal and distal ends, and at least a first lumen;

at least a first drug delivery device within the first lumen of the catheter jacket, the drug delivery device having proximal and distal ends;

a deflection mechanism at the proximal end of the catheter operatively attached to a deflector device at the distal end of the catheter jacket, activation of the deflector device by movement of the deflection mechanism deflects the distal end of the catheter jacket and the drug delivery device therein; and a tip alignment mechanism operatively attached to the deflection mechanism and the proximal end of the drug delivery device, the tip alignment mechanism comprising at least one relative movement compensation mechanism selected from the group consisting of a rotatable differential screw mechanism, a gear mechanism, a cam mechanism, a threaded mechanism, and a grooved mechanism, wherein movement of the deflection mechanism causes simultaneous compensating movement of the relative movement compensation mechanism.

* * * * *